United States Patent [19]

Tadanier et al.

[11] 4,230,846
[45] Oct. 28, 1980

[54] 1,5-CARBAMATES OF FORTIMICIN B AND DERIVATIVES

[75] Inventors: John S. Tadanier; Jerry R. Martin, both of Waukegan, Ill.

[73] Assignee: Abbott Laboratories, North Chicago, Ill.

[21] Appl. No.: 79,133

[22] Filed: Sep. 26, 1979

[51] Int. Cl.³ .............................................. C07H 17/00
[52] U.S. Cl. ..................................... 536/4; 536/17 R; 544/92; 424/180
[58] Field of Search ................... 536/4, 17; 544/92; 424/180, 181

[56] References Cited

U.S. PATENT DOCUMENTS

| | | | |
|---|---|---|---|
| 4,091,032 | 5/1979 | Tadanier et al. | 260/345.8 R |
| 4,124,756 | 11/1978 | Martin et al. | 536/17 R |
| 4,169,198 | 9/1979 | Martin et al. | 536/17 R |
| 4,176,617 | 11/1979 | Martin et al. | 424/180 |
| 4,183,920 | 1/1980 | Kurath et al. | 424/180 |
| 4,187,296 | 2/1980 | Tadanier et al. | 424/180 |
| 4,187,297 | 2/1980 | Martin et al. | 424/180 |
| 4,187,298 | 2/1980 | McAlpine | 536/17 R |
| 4,187,299 | 2/1980 | Post | 536/17 R |

Primary Examiner—John D. Randolph
Attorney, Agent, or Firm—Gildo E. Fato; Robert L. Niblack; Joyce R. Niblack

[57] ABSTRACT

A 1,5-fortimicin B carbamate represented by the formula:

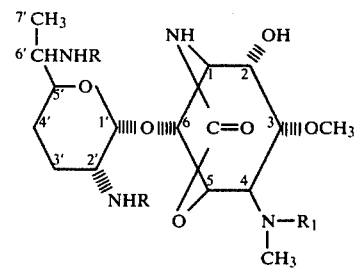

wherein each R is hydrogen or monocyclicaryloxycarbonyl and $R_1$ is selected from the group consisting of: loweralkyl, hydroxyloweralkyl, hydrogen, aminoloweralkyl, N-loweralkylaminoloweralkyl, N,N-diloweralkylaminoloweralkyl, trihaloalkoxycarbonyl, an amino acid residue and an N-protected amino acid residue and the pharmaceutically acceptable salts thereof.

14 Claims, No Drawings

1,5-CARBAMATES OF FORTIMICIN B AND DERIVATIVES

BACKGROUND OF THE INVENTION

Aminoglycoside antibiotics are a useful class of antibiotics which include streptomycins, kanamycins, neomycins, gentamicins, tobramycins, amikacin, and the more recently discovered fortimicins. It is known that the antibacterial and pharmacological properties of many of the naturally produced aminoglycoside antibiotics can be advantageously altered by structural modifications. For example, certain chemical modifications in the gentamicin and kanamycin family of antibiotics provide compounds which are less toxic than the parent antibiotic. Further, certain modifications in the gentamicin and kanamycin series have been found to alter the antibacterial spectrum advantageously either by increasing the intrinsic activity or increasing activity against resistant strains.

Chemical modification has also been found to be of value in the fortimicin family of aminoglycoside antibiotics as well. See for example U.S. Pat. Nos. 4,901,032 and 4,124,756 and commonly assigned, copending application Ser. Nos. 863,006 now U.S. Pat. No. 4,192,867 issued Mar. 11, 1980 and 863,009 (now U.S. Pat. No. 4,169,198), filed Dec. 21, 1977, issued Mar. 11, 1980, directed to the valuable class of fortimicins, 2-deoxyfortimicins.

The present invention provides intermediates which are useful in preparing 2-deoxyfortimicin B, disclosed and claimed in allowed, copending, commonly assigned application U.S. Ser. No. 863,009, filed Dec. 27, 1977, now U.S. Pat. No. 4,169,198.

SUMMARY OF THE INVENTION

The present invention provides 1,5-carbamates of fortimicin B and fortimicin B derivatives. The compounds are useful as intermediates for synthesizing 2-deoxyfortimicin B and 2-deoxyfortimicin B derivatives.

DETAILED DESCRIPTION OF PREFERRED EMBODIMENTS

The present invention provides fortimicin B-1,5-carbamates which are useful as intermediates in the preparation of 2-deoxyfortimicin B and derivatives thereof.

The compounds of this invention are represented by the formula:

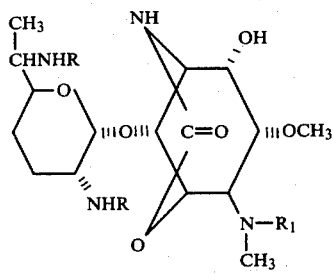

wherein each R is hydrogen or monocyclicaryloxycarbonyl and $R_1$ is selected from the group consisting of loweralkyl, hydroxyloweralkyl, hydrogen, aminoloweralkyl, N-loweralkylaminoalkyl, N,N-diloweralkylaminoloweralkyl, trihaloalkoxycarbonyl, an amino acid residue and an N-protected amino acid residue, and the pharmaceutically acceptable salts thereof.

When R is hydrogen, the carbamates are useful as analytical samples for confirming the identity of the compounds wherein R is monocyclicaryloxycarbonyl, such as benzyloxycarbonyl, Compounds where R is monocyclic aryloxycarbonyl are intermediates useful in preparing 2-deoxyfortimicin B and 2-deoxyfortimicin B derivatives.

The term "loweralkyl", as used herein, refers to straight or branched chaim alkyl radicals containing from 1 to 6 carbon atoms including, but not limited to methyl, ethyl, n-propyl, iso-propyl, n-butyl, sec-butyl, tert-butyl, n-pentyl, 1-methylbutyl, 2-methylbutyl, 3-methylbutyl, 2,2-dimethylpropyl, n-hexyl, 1-methylpentyl, 2-methylpentyl, 3-methylpentyl, 2,2-dimethylbutyl, etc.

The term "hydroxyloweralkyl" refers to a $C_2$–$C_6$ alkyl radical as defined above and having one or more hydrogen atoms replaced by a hydroxyl radical, such as 1-hydroxyethyl, 2-hydroxy-n-propyl, and the like.

The term "aminoloweralkyl" refers to amino groups $RNH_2$ wherein R is a loweralkyl radical as defined above.

The terms N-loweralkylaminoloweralkyl and N,N-diloweralkylaminoloweralkyl refer to amino groups so substituted with loweralkyl groups as defined above such as methylaminoethyl, dimethylaminoethyl, etc.

The term "trihaloalkoxycarbonyl" refers to a loweralkoxycarbonyl moiety containing three halo substitutents. "Lower alkoxy" refers to alkoxy groups containing from 1 to 6 carbon atoms, i.e. methoxy, ethoxy, propoxy, butyryloxy, etc. "Halo" refers to chloro, fluoro, bromo or iodo. Representative trihaloalkoxycarbonyl groups include, but are not limited to trifluoromethoxycarbonyl,2,2,2-trichloroethoxycarbonyl, etc.

The term "amino acid residue" refers to a residue of a naturally occuring amino acids such as glycyl, alanyl, valyl, threonyl, leucyl, iso-leucyl, prolyl, sarcosyl, histidyl, tyrosyl, phenylalanyl, methionyl, seryl, lysyl, asparaginyl, threonyl, glutaminyl, glutamyl and 2-hydroxy-4-aminobutyryl and the like having either or both the N-terminus hydrogen and/or the C-terminus hydroxy radical cleaved. The amino acid residues can be in the D or L configurations or mixtures thereof and, unless otherwise specified are, in accordance with accepted convention, in the L-configuration.

The term "N-protected amino acid residue" refers to the above amino acid radicals protected at the N-terminus by a suitable protecting group such as monocyclicaryloxycarbonyl protecting group.

The term "monocyclicaryloxycarbonyl" refers to common amine protecting groups such as benzyloxycarbonyl(Z), p-methylbenzyl, p-methoxybenzyl, o-nitrobenzyl and the like.

The term "pharmaceutically acceptable salts" refers to the non-toxic acid addition salts which are generally prepared either in situ or by reacting a compound of this invention with a suitable organic or inorganic acid. Representatives salts include the mono or suitable per salts such as the hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, napsylate, etc.

The carbamates of this invention, when R is acyl and $R_1$ is alkyl are useful as intermediates in the synthesis of 2-deoxyfortimicin B which not only exhibits anti-bacterial activity of its own, but is also a valuable intermediate in the synthesis of 2-deoxyfortimicin A as set forth in commonly assigned, copending application Ser. No. 863,006, filed Dec. 21, 1977. The in vitro activity of 2-deoxyfortimicin As set forth in Table I. The in vitro activity of 2-deoxyfortiicin A tetrahydrochloride, fortimicin A disulfate and fortimicin A tetrahydrochloride were determined using a 2-fold agar dilution method using 10 ml per petri plate of Mueller-Hinton agar. The agar was inoculated with one loopful (0.001 ml/loop) of a 1:10 dilution of a 24 hour broth culture of the indicated test organism and incubated at 37° C. for 24 hours.

TABLE I

In Vitro Antimicrobial Activity of 2-Deoxyfortimicin A.4 HCl

| Microorganism | Minimum inhibitory concentration (mcg/ml) | | |
|---|---|---|---|
| | Fortimicin A di-Sulfate | Fortimicin A tetra-hydrochloride | 2-deoxyfortimicin A tetra-hydrochloride |
| Staph. aureus Smith | 0.78 | 0.78 | 0.78 |
| Strep. faecalis 10541 | 50 | 50 | 50 |
| Enterobacter aerogenes 13048 | 3.1 | 3.1 | 3.1 |
| E. coli Juhl | 6.2 | 6.2 | 6.2 |
| E. coli BL 3676 (Res) | 25 | 25 | 25 |
| Kleb. pneumoniae 10031 | 3.1 | 1.56 | 1.56 |
| Kleb. pneumoniae KY 4262 | 6.2 | 3.1 | 6.2 |
| Providencia 1577 | 3.1 | 3.1 | 3.1 |

TABLE I-continued

In Vitro Antimicrobial Activity of 2-Deoxyfortimicin A.4 HCl

| Microorganism | Minimum inhibitory concentration (mcg/ml) | | |
|---|---|---|---|
| | Fortimicin A di-Sulfate | Fortimicin A tetra-hydrochloride | 2-deoxyfortimicin A tetra-hydrochloride |
| Pseudo. aeruginosa BMH #10 | 0.78 | 0.78 | 0.78 |
| Pseudo aeruginosa KY 8512 | 12.5 | 25 | 12.5 |
| Psuedo. aeruginosa KY 8516 | 50 | 100 | 50 |
| Psuedo. aeruginosa 209 | >100 | >100 | >100 |
| Psuedo. aeruginosa 27853 | 12.5 | 25 | 12.5 |
| Sal. typhimurium Ed. #9 | 1.56 | 1.56 | 1.56 |
| Serratis marcescens 4003 | 1.56 | 3.1 | 3.1 |
| Shigella sonnei 9290 | 6.2 | 12.5 | 6.2 |
| Proteus rettigeri U6333 | 12.5 | 25 | 25 |
| Proteus vulgaris JJ | 6.2 | 6.2 | 3.1 |
| Proteus mirabilis Fin. #9 | 6.2 | 6.2 | 6.2 |
| E coli 76-2 | 6.2 | 3.1 | 3.1 |

The general synthetic routes for preparing the compounds of this invention are set forth in the following reaction schemes and the synthesis of representative compounds is illustrated in detail in the Examples. For ease of reference, reference numerals have been assigned to each compound in the reaction schemes and the reference numerals have been used in the Examples following the compound names.

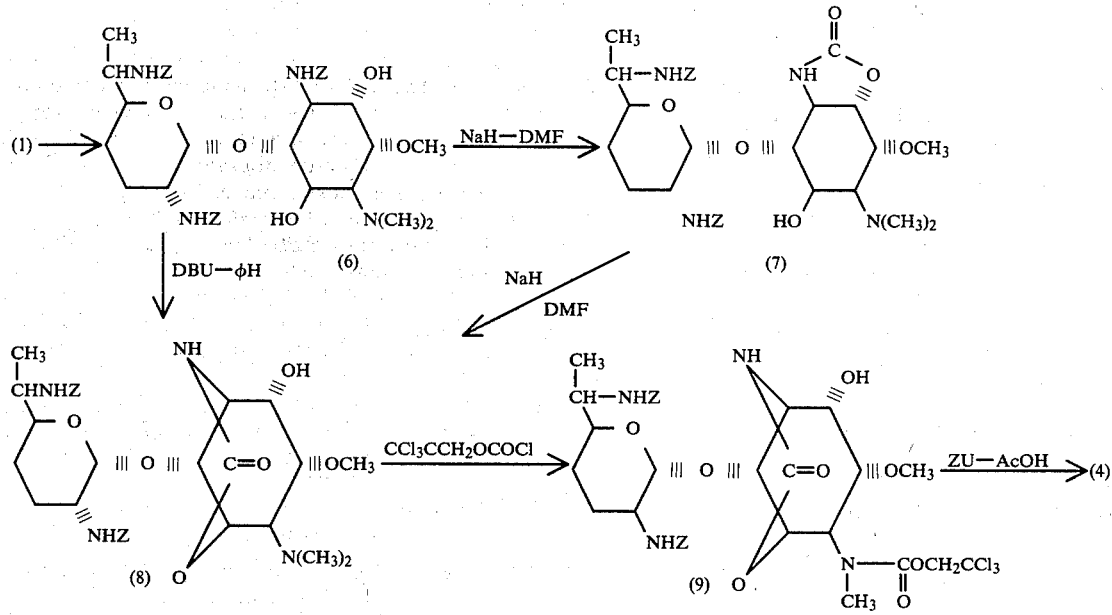

The following Examples further illustrate the present invention.

EXAMPLE 1

1,2',6'-Tri-N-benzyloxycarbonylfortimicin B(1)

To a stirred solution of 2.0 g of fortimicin B, 30 ml of water and 60 ml of methanol, cooled in an ice bath, is added 4.44 g of N-(benzyloxycarbonyloxy)succinimide. Stirring is continued at 0° C. for 3 hours and then at room temperature for 22 hours. The major portion of the methanol is evaporated under reduced pressure and the residue is shaken with a mixture of chloroform and water. The chloroform solution is washed with water and dried over anhydrous magnesium sulfate. The chloroform is evaporated and the residue is chromatographed on silica gel. Elution with a solvent system composed of chloroform-methanol-ammonium hydroxide [23.4:1.4:0.1 (v/v/v)] gives 1.05 g of product (1): $[\alpha]_D^{25} -16.5°$ (c 1.0, $CH_3OH$); IR($CDCl_3$) 1712 and 1507 cm$^{-1}$; NMR($CDCl_3$) $\delta 1.03$ ($C_6'$—$CH_3, J_{6'7'}=6.0$ Hz), 2.32($C_4$—$NCH_3$), 3.41($OCH_3$).

Analysis Calcd. for $C_{39}H_{50}N_4O_{11}$: C, 62.39; H, 6.71; N, 7.46. Found: C, 62.16; H, 6.76; N, 7.43.

EXAMPLE 2

Tetra-N-benzyloxyloxycarbonylfortimicin A(2)

To a magnetically stirred solution of 1.00 g of 1,2',6'-tri-N-benzyloxycarbonylfortimicin B, 0.357 g of N-benzyloxycarbonylglycine and 0.376 g of 1-hydroxybenzotriazole monohydrate in 2.8 ml of tetrahydrofuran, cooled to 0° C. in an ice bath, is added a solution of 0.353 g of N,N-dicyclohexylcarbodiimide in 2.8 ml of tetrahydrofuran. An additional 2.8 ml of tetrahydrofuran is added to rinse all the N,N-diclyclohexylcarbodiimide into the reaction vessel. Stirring is continued at 0° C. for 1 hour and then at ambient temperature for 18 hours. The precipitated N,N'-dicyclohexylurea is removed by filtration. The tetrahydrofuran is evaporated from the filtrate under reduced pressure leaving 1.79 g of product. A sample (1.20 g) is chromatographed on a column of silica gel, prepared and eluted with a solvent system consisting of benzene-methanol-95% ethanol-concentrated ammonium hydroxide (23.5:1.4:2.0:0.2 u/u/u/u). Fractions containing the desired product were combined and concentrated under reduced pressure leaving 0.826 g. of tetra-N-benzyloxycarbonylfortimicin A: $[\alpha]_D^{23} +52.9°$ (c 1.0, $CH_3OH$); IR 1710, 1635, 1500 cm$^{-1}$; NMR ($CDCl_3$)$\delta 1.16$ ($C_6'$—$CH_3$, J=6.5), 2.82 ($C_4$—$NCH_3$), 3.31 ($OCH_3$), 4.80 ($H_1'$, J=3.0).

Analysis Calcd. for: $C_{49}H_{59}N_5O_{14}$: C, 62.48; H, 6.31; N, 7.43. Found: C, 62.52; H, 6.49; N, 7.23.

B. To a magnetically stirred solution of 4.02 g. of 1,2',6'-tri-N-benzyloxycarbonylfortimicin B in 40 ml. of tetrahydrofuran, cooled to 0° in an ice bath, was added 1.80 g. of the N-hydroxysuccinimide ester of N-benzyloxy-carbonylglycine. Stirring was continued at 0° for 4 hours and then at room temperature for 23 hours. The resulting solution was shaken with a mixture of 300 ml. of $CHCl_3$ and 400 ml. of 5% aqueous $NaHCO_3$ solution. The $CHCl_3$ solution was separated and washed with 400 ml. of water. The aqueous solutions were washed in series with three 200 ml. portions of $CHCl_3$. The $CHCl_3$ was evaporated under reduced pressure to yield 5.18 g. of a white glass. This product was chromatographed on a column of 250 g. of silica gel (3.4×74 cm.). Elution was carried out with a solvent system composed of benzene-methanol-ethanol-ammonium hydroxide (23.5:1.60:1.80:0.20 v/v). The fractions containing the product were combined, and evaporation of the solvent left 4.58 g. of tetra-N-benzyloxycarbonylfortimicin A (2) identical with that prepared as described above.

EXAMPLE 3

2',6'-Di-N-benzyloxycarbonylfortimicin B-1, 2-carbamate (3)

A. 1,2',6'-Tri-N-benzyloxycarbonylfortimicin B-4,5-formaldehyde oxazolidine

A solution of 16.0 g of 1,2',6'-tri-N-benzyloxycarbonylfortimicin B (1), 8 ml of 37% aqueous formaldehyde, and 400 ml of methanol is allowed to stand overnight at room temperature. The major portion of the solvent is evaporated under reduced pressure. Residual water is removed by co-distillation with benzene leaving 16.3 g of the desired product as a white glass: NMR(CDl$_3$) δ1 17 d (J=6.5 Hz) (C$_6'$—CH$_3$), 2.28 (NCH$_3$), 2.80 q (J$_{3,4}$=6.5 Hz, J$_{4,5}$=2.0 Hz) (C$_4$—H); 3.5 (OCH$_3$); 3.81 d, 4.60 d (OCH$_2$—N) (J=2.3 Hz).

B. 2',6'-Di-N-benzyloxycarbonylfortimicin B-1, 2-carbamate 4,5-formaldehyde oxazolidine A solution of 16.3 g of the above-prepared oxazolidine intermediate, 16.3 g of 1,5-diazobicyclo [5.4.0] undecene-5, and 815 ml of benzene is heated under reflux for four days. The resulting solution is cooled to room temperature, 250 ml of water are added and the mixture stirred at room temperature for one hour. The mixture is then shaken with 700 ml of 5 percent aqueous sodium bicarbonate. The aqueous phase is separated and extracted with 500 ml of benzene. The benzene solutions are washed with three 500 ml portions of saturated aqueous sodium chloride, combined and dried over magnesium sulfate. Evaporation of the benzene under reduced pressure yields 15.3 g of the desired product: IR (CDCl$_3$) 3459,1762,1709 cm$^{-1}$.

C. 2',6'-Di-N-benzyloxycarbonylfortimicin B-1, 2-carbamate (3)

A solution of 15.3 g of the above-prepared intermediate, 5.2 g of hydroxylamine hydrochloride, 14.5 ml of acetic acid and 900 ml of methanol are heated under reflux for 1 hour. The solution is cooled to room temperature and the major portion of the methanol evaporated under reduced pressure. The residue is shaken with a mixture of one liter of chloroform and one liter of 1:1 (v/v) concentrated ammonium hydroxide-water. The aqueous layer is separated and the chloroform solution is washed with 500 ml of water. The aqueous layer is separated and the chloroform solution is washed with 500 ml of water. The aqueous solutions are extracted with 500 ml of chloroform. The chloroform solutions are combined and dried over magnesium sulfate. Evaporation of the chloroform under reduced pressure leaves 14.8 g of crude 2'6'-di-N-benzyloxycarbonylfortimicin B 1,2-carbamate (3). The latter is chromatographed on a column of 850 g of silica gel, packed and eluted with a solvent system prepared from chloroform-methanol [19.5-0.5(v/v)] to yield 7.9 g of pure product: [α]$_D^{21}$+27° (c 1%, CH$_3$OH); NMR (CDCl$_3$) δ1.14 d (J=6.5 Hz) (C$_6'$—CH$_3$), 2.39 (NCH$_3$), 3.45 (OCH$_3$); IR(CDCl$_3$) 3439, 3411, 3353, 1765, 1705 cm$^{-1}$.

EXAMPLE 4

2',6',2''-Tri-N-benzyloxycarbonylfortimicin A-1, 5-carbamate (5)

A solution of 4.04 g of tetra-N-benzyloxycarbonylfortimicin A (2), 4.0 g of 1,5-diazabicyclo [5.4.0] undecene-5, and 200 ml of benzene is heated under reflux for six days. The solution is cooled to room temperature, water (100 ml) is added, and the resulting mixture is stirred at room temperature during which time a benzene-insoluble, tarry material separates. The supernatant is decanted and shaken with a mixture of 300 ml of benzene and 300 ml of five percent aqueous sodium bicarbonate. The aqueous solution is separated and extracted with 300 ml of benzene. The benzene solutions are washed and combined.

The benzene-insoluble material is taken up in 200 ml of chloroform, and the chloroform solution is washed twice with 200 ml portions of water. The aqueous solutions are washed in series with two 100 ml portions of chloroform. The chloroform solutions are combined with the benzene solutions, and the solvent is evaporated under reduced pressure leaving 3.93 g of brown glass. The product is chromatographed on a column of 200 g of silica gel packed and eluted with a solvent system composed of ethyl acetate-isopropanol [19:1 (v/v)]. Early portions yield 0.9539 g of starting material (2). Later fractions yield 0.892 of product (5): [α]$_D^{23}$+59° (c 1%, CH$_3$OH): NMR (CDCl$_3$) δ1.19 d (J=6.4 HZ) (C$_6'$—CH$_3$); 3.00, 3.04 (NCH$_3$, rotamers); 3.45, 3.51 (OCH$_3$, rotamers); IR(CDCl$_3$) 3522, 3437, 3332, 1712,1644 cm$^{-1}$.

Analysis Calcd. for C$_{42}$H$_{51}$N$_5$O$_{13}$: C, 60.49; H, 6.16; N, 8.40. Found: C, 59.31; H, 6.15; N, 8.32.

EXAMPLE 5

2,6'-Di-N-benzyloxycarbonylfortimicin B-1,5-carbamate (4)

A solution of 7.22 g of crude 2',6'-di-N-benzyloxycarbonylfortimicin B-1,2-carbamate (3), prepared via cyclizazation of 1,2',6''-tri-N-benzyloxycarbonylfortimicin B-4,5-formaldehyde oxazolidine with 1,5-diazabicyclo [5.4.0] undecene-5 in refluxing benzene as described in Example 3, 360 ml of methanol and 180 ml of 1:4 (v/v) concentrated ammonium hydroxide-water, is kept at room temperature for two days. The major portion of the methanol is evaporated under reduced pressure, and the residue is shaken with a mixture of 300 ml of chloroform and 400 ml of 5 percent aqueous sodium bicarbonate. The chloroform solution is separated and washed with 400 ml of water. The aqueous solutions are washed in series with three 200 ml portions of chloroform. The chloroform solutions are combined and the chloroform is evaporated under reduced pressure leaving 7.0 g of light orange glass. Chromatography of the latter on a column of 450 g of silica gel packed and eluted with a solvent system composed of methylene chloride-methanol-concentrated ammonium hydroxide [20:2:0.1 (v/v/v)] gave 3.26 g of pure 2,6'-di-N-benzyloxycarbonylfortimicin B-1,5-carbamate (4): [α]$_D^{23}$+101° (c 1%, CH$_3$OH), NMR(CDCl$_3$) δ1.14 d (J=3 Hz) (C$_6'$—CH$_3$), 2.36 (NHCH$_3$), 3.45 (OCH$_3$), IR(CDCl$_3$) 3529, 3439, 3324, 1712 cm$^{-1}$.

Analysis Calcd. for C$_{32}$H$_{42}$N$_4$O$_{10}$: C, 59.80; H, 6.59; N, 8.72. Found: C, 59.43; H, 6.72; N, 8.63.

EXAMPLE 6

4-N-Methyl-1,2',6'-tri-N-benzyloxycarbonylfortimicin B (6)

A magnetically stirred solution of 10 g of 1,2',6'-tri-N-benzyloxycarbonylfortimicin B (1), 750 ml of methanol, 225 ml of Sorensen's buffer (pH 6), and 25 ml of formalin is kept at room temperature for 50 minutes. Sodium cyanoborohydride (2.54 g) is added, and stirring is continued at room temperature for 20 hours. The major portion of the methanol is evaporated under reduced pressure and the residue is shaken with a mixture of 400 ml of chloroform and 400 ml of 5 percent aqueous sodium bicarbonate. The chloroform solution is separated and washed with 500 ml of water. The aqueous solutions are washed in series with three 200 ml portions of chloroform. The chloroform solutions are combined and dried over magnesium sulfate. The chloroform is evaporated under reduced pressure leaving 10.2 g of 4-N-methyl-1,2',6'-tri-N-benzyloxycarbonylfortimicin B (6): NMR (CDCl$_3$): δ1.00 (J=6.7 Hz) (C$_6'$—CH$_3$), 2.36 N(CH$_3$)$_2$; 3.39 (OCH$_3$).

EXAMPLE 7

4-N-Methyl-2',6'-di-N-benzyloxycarbonylfortimicin B-1,2-carbamate (7)

To a magnetically stirred solution of 1.01 g of 4-N-methyl-1,2',6'-tri-N-benzyloxycarbonylfortimicin B (6) in 20 ml of dry N,N-dimethylformamide, cooled in an ice bath under a nitrogen atmosphere, is added 0.2843 g of a 57 percent oily dispersion of sodium hydride. Stirring is continued at 0° for one hour. The ice bath is removed and the reaction mixture is kept at ambient temperature for 22 hours during which time a gel forms. A solution of 0.8 ml of acetic acid in 2 ml of water is added to the cooled gel, and the resulting mixture is shaken with a mixture of 100 ml of chloroform and 200 ml of 5 percent aqueous sodium carbonate. The chloroform solution is separated and washed with 200 ml of water. The aqueous solutions are washed in series with three 100 ml portions of chloroform. The chloroform solutions are combined and the chloroform is evaporated under reduced pressure. Residual N,N-dimethylformamide is removed by co-distillation with toluene under reduced pressure to yield 0.930 g of crude 4-N-methyl-2'6'-di-N-benzyloxycarbonylfortimicin B-1,2-carbamate (7). Chromatography of the latter on a column of 80 g of silica gel packed and eluted with a solvent system composed of 1,2-dichloroethane-methanol-concentrated ammonium hydroxide [23.4:1.4:0.1 (v/v/v)] gave 0.384 g of pure product (7): NMR δ1.17 d(J=7.2 Hz)(C$_6'$—CH$_3$), 2.46(N(CH$_3$)$_2$), 3.47(OCH$_3$). IR 3443,3313,1765,1713 cm$^{-1}$.

Analysis Calcd. for: C$_{33}$H$_{45}$N$_4$O$_{10}$: C, 60.25; H, 6.75; N, 8.53. Found: C, 60.18; H, 6.75; N, 8.88.

EXAMPLE 8

4-N-Methyl-2',6'-di-N-benzyloxycarbonylfortimicin B-1,5-carbamate (8)

A solution prepared from 3.04 g of 4-N-methyl-1,2',6'-tri-N-benzyloxycarbonylfortimicin B (6), 3 g of 1,5-diazabicyclo [5.4.0] undecene-5, and 150 ml of benzene is heated under reflux for six days. The solution is cooled to room temperature, 100 ml of water is added and the resulting mixture is stirred at room temperature for one hour and then shaken with a mixture of 400 ml of 5 percent aqueous sodium bicarbonate and 300 ml of chloroform. The latter is chromatographed on a column of 260 mg of silica gel prepared and eluted with a solvent system composed of 1,2-dichloroethane-methanol-concentrated ammonium hydroxide [23.4:1.4:0.1 (v/v/v)]. Early fractions gave 0.40 g of starting material (6). Later fractions gave 1.00 g of product (8) as a white glass: [α]$_D^{23}$+83° (c 1%, CH$_3$OH); NMR δ1.16 d (J=7 Hz) (C$_6'$—CH$_3$), 2.42 (N(CH$_3$)$_2$), 3.44 (OCH$_3$), IR 3518, 3438, 3318, 1710 cm$^{-1}$.

Analysis Calcd. for C$_{33}$H$_{45}$N$_4$O$_{10}$: C, 60.25; H, 6.75; N, 8.53. Found: C, 59.78; H, 6.68; N, 8.24.

EXAMPLE 9

4-N-Methyl-2',6'-di-N-benzyloxycarbonylfortimicin B-1,5-carbamate (8). Alternate Method To a magnetically stirred solution of 9.48 g of crude 4-N-methyl-2',6'-di-N-benzyloxycarbonylfortimicin B-1,2-carbamate (7), prepared as described in Example, in 470 ml of methanol is added 235 ml of 1:4 (v/v) concentrated ammonium hydroxide-water solution. The resulting solution is stirred at ambient temperature for three days. The major portion of the methanol is evaporated under reduced pressure, and the residue is shaken with a mixture of 400 ml of 5 percent aqueous sodium bicarbonate and 300 ml of chloroform. The chloroform solution is separated and washed with 400 ml of 5 percent aqueous sodium chloride. The aqueous solutions are washed in series with four 200 ml portions of chloroform. The chloroform solutions are combined and dried over magnesium sulfate. Evaporation of the chloroform under reduced pressure left 8.69 g of a light brown glass. Chromatography of the latter on a column of 450 g of silica gel packed and eluted with a solvent system composed of ethyl acetate-ethanol-triethylamine [18.5:1.5:0.1 (v/v/v)] gave 5.39 g of pure 4-N-methyl-2',6'-di-N-benzyloxycarbonylfortimicin B-1,5-carbamate (8) identical with that described in Example 8.

EXAMPLE 10

4-N-(2,2,2-Trichloroethoxycarbonyl)-2',6'-di-N-benzyloxycarbonylfortimicin B-1,5-carbamate (9)

A solution prepared from 0.882 g of 4-N-methyl-2',6'-di-N-benzyloxycarbonylfortimicin B-1,5-carbamate (8), 0.3065 g of anhydrous potassium carbonate, 0.4102 g of 2,2,2-trichloroethoxycarbonyl chloride, and 50 ml of benzene is heated under reflux with magnetic stirring for 6 hours. The resulting mixture is cooled to room temperature and shaken with a mixture of 150 ml of benzene and 200 ml of 0.5 N ammonium hydroxide. The aqueous solution is separated and extracted with 200 ml of benzene. The benzene solutions are washed in series with three 200 ml portions of water and combined. Evaporation of the benzene under reduced pressure leaves 0.910 g of a white glass. The latter product was chromatographed on a column of 80 g of silica gel prepared and eluted with a solvent system composed of methylene chloride-methanol [23.4:1.4 (v/v)] to yield 0.586 g of 4-N-(2,2,2-trichloroethoxycarbonyl)-2',6'-di-N-benzyloxycarbonylfortimicin B-1,5-carbamate (9): NMR (CDCl$_3$); δ1.18 d (J=7 Hz) (C$_6'$—CH$_3$); 3.10 (NCH$_3$); b 3.45 (OCH$_3$); IR 3530, 3438, 1704 cm$^{-1}$.

Analysis Calcd for C$_{35}$H$_{43}$N$_4$O$_{12}$Cl$_3$: C, 51.38; H, 5.30; N, 6.85. Found: C, 51.12; H, 5.38; N, 6.79.

EXAMPLE 11

4-N-(2,2,2-Trichloroethoxycarbonyl)-2'6'-di-N-benzyloxycarbonylfortimicin B-1,5-carbamate (9). Alternate method To a magnetically stirred solution of 0.400 g of 2',6'-di-N-benzyloxycarbonylfortimicin B-1,5-carbamate (4) in 6 ml of tetrahydrofuran is added 0.198 g of N-(2,2,2-trichloroethoxycarbonyloxy) succinimide. Stirring is continued at ambient temperature overnight. The resulting solution is shaken with a mixture of 100 ml of chloroform and 100 ml of 5 percent aqueous sodium bicarbonate. The chloroform solutions are combined and the chloroform is evaporated to leave 0.539 g of white glass. Chromatograph of 0.489 g of the latter on a column of silica gel packed and eluted with ethyl acetate gave 0.411 g of 4-N-(2,2,2-trichloroethoxycarbonyl)-2',6'-di-N-benzyloxycarbonylfortimicin B-1,2-carbamate (9) identical with that obtained in Example 10.

The 1,5-carbamates of this invention are useful as intermediates in preparing 2-deoxyfortimicin B, which is the subject of an allowed claim of U.S. patent application, Ser. No. 863,009, filed Dec. 21, 1977.

2-Deoxyfortimicin B can be prepared from a 1,5-carbamate of this invention using a general procedure developed by D. H. L. Barton et al., *J. Chem Soc*, Perkin I,1574(1975). Generally speaking, treatment of an 4-N-acylated-2',6'-di-N-acylated fortimicin B-1,5-carbamate, such as 4-N-acetyl-2',6'-di-N-trichloroethoxycarbonyl-2',6'-di-N-benzyloxycarbonylfortimicin B-1,5-carbamate or 2',6',2''-tri-N-benzyloxycarbonylfortimicin A-1,5-carbamate with thiocarbonyldiimidazole in an inert solvent such as tetrahydrofuran, preferably in the presence of a tertiary amine such as triethylamine, gives the 2-O-thiocarbonylimidazole ester. Reduction with tri-N-butylstannane gives 2-deoxyfortimicin B-1,5-carbamate. Alkaline hydrolysis of the latter with, for example, potassium hydroxide in aqueous ethanol gives 2-deoxyfortimicin B.

4-N-derivatives of 2-deoxyfortimicin B can similarly be prepared by selecting the appropriate 4-N-substituted carbamate.

The unprotected carbamates (R is hydrogen) are useful as analytical samples to confirm the identity of the intermediates of this invention (R is benzyloxycarbonyl or another suitable aryloxycarbonyl) protecting group.

EXAMPLE 12

2',6'-Di-N-benzyloxycarbonylfortimicin B-1,5-carbamate (14)

A suspension of 0.378 g of 4-N-(2,2,2-trichloroethoxycarbonyl)-2',6'-di-N-benzyloxycarbonylfortimicin B-1,5-carbamate (9) prepared as described in example 10, 1.21 g of zinc dust, and 7 ml of acetic acid is stirred at room temperature for 6 hr. This zinc is removed by filtration and washed with 30 ml of ethanol. The filtrate and ethanol washings are combined and shaken with a mixture of 200 ml of 10% aqueous NaCl solution and 100 ml of CHCl$_3$. The CHCl$_3$ solution is separated and washed with 200 ml of 5% aqueous NaCHO$_3$ solution. The aqueous solutions are washed in series with two 100-ml portions of CHCl$_3$ solutions are combined and dried (MgSO$_4$). Evaporation of the CHCl$_3$ leaves 0.247 g of 2',6'-di-N-benzyloxycarbonylfortimicin B-1,5-carbamate (4), identical with material prepared as described in example 5.

We claim:

1. A 1,5-fortimicin B carbamate represented by the formula:

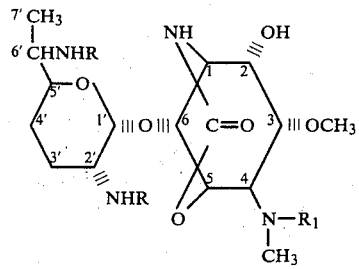

wherein each R is hydrogen or benzyloxycarbonyl and R$_1$ is selected from the group consisting of: loweralkyl, hydroxyloweralkyl, hydrogen, aminoloweralkyl, N-loweralkylaminoloweralkyl, N,N-diloweralkylaminoloweralkyl, trihaloalkoxycarbonyl, an amino acid residue and an N-protected amino acid residue and the pharmaceutically acceptable salts thereof.

2. A compound of claim 1 wherein R$_1$ is loweralkyl.

3. A compound of claim 2 wherein R$_1$ is methyl.

4. A compound of claim 2 wherein R$_1$ is ethyl.

5. A compound of claim 1 wherein R$_1$ is trihaloalkoxycarbonyl.

6. A compound of claim 5 wherein R$_1$ is trichloroethoxycaronyl.

7. A compound of claim 1 wherein R$_1$ is an N-protected amino acid residue.

8. A compound of claim 6 wherein R$_1$ is N-benzyloxyglycyl.

9. A compound of claim 8 wherein each R is also benzyloxycarbonyl: 2,6',2''-tri-N-benzyloxyfortimicin A-1,5-carbamate.

10. A compound of claim 1 wherein R$_1$ is hydrogen.

11. A compound of claim 10: 2',6'-di-N-benzyloxycarbonylfortimicin B-1,5-carbamate.

12. A compound of claim 10: fortimicin B-1,5-carbamate or a salt thereof.

13. A compound of claim 3: 4-N-methyl-2',6'-tri-N-benzyloxycarbonylfortimicin B-1,5-carbamate.

14. A compound of claim 6: 4-N-(2,2,2-trichloroethoxycarbonyl)-2',6'-di-N-benzyloxycarbonyl fortimicin B-1,5-carbamate.

* * * * *